US006639082B2

(12) United States Patent
Polniaszek et al.

(10) Patent No.: US 6,639,082 B2
(45) Date of Patent: Oct. 28, 2003

(54) METHODS FOR THE PREPARATION OF BIPHENYL ISOXAZOLE SULFONAMIDES

(75) Inventors: Richard P. Polniaszek, Foster City, CA (US); Xuebao Wang, East Brunswick, NJ (US); John K. Thottathil, Ivanhoe, IL (US); Theodor Denzel, Regensburg (DE)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 09/967,387

(22) Filed: Sep. 28, 2001

(65) Prior Publication Data

US 2002/0132838 A1 Sep. 19, 2002

Related U.S. Application Data

(60) Provisional application No. 60/240,902, filed on Oct. 17, 2000.

(51) Int. Cl.⁷ ............................................. C07D 413/12
(52) U.S. Cl. ........................................................ 548/235
(58) Field of Search ................................... 548/235

(56) References Cited

U.S. PATENT DOCUMENTS

| | | | |
|---|---|---|---|
| 2,888,455 A | 5/1959 | Kano | |
| 5,236,928 A | 8/1993 | Chakravarty et al. | |
| 5,270,313 A | 12/1993 | Burri et al. | |
| 5,292,740 A | 3/1994 | Burri et al. | |
| 5,378,715 A | 1/1995 | Stein et al. | |
| 5,464,853 A | 11/1995 | Chan et al. | |
| 5,514,691 A | 5/1996 | Chan et al. | |
| 5,514,696 A | 5/1996 | Murugesan et al. | |
| 5,571,821 A | 11/1996 | Chan et al. | |
| 5,591,761 A | 1/1997 | Chan et al. | |
| 5,594,021 A | 1/1997 | Chan et al. | |
| 5,612,359 A | 3/1997 | Murugesan | |
| 5,760,038 A | 6/1998 | Murugesan et al. | |
| 5,780,473 A | 7/1998 | Murugesan et al. | |
| 5,827,869 A | 10/1998 | Murugesan | |
| 5,846,990 A | 12/1998 | Murugesan et al. | |
| 5,856,507 A | 1/1999 | Polniaszek et al. | 548/241 |
| 5,939,446 A | 8/1999 | Murugesan et al. | |
| 5,965,732 A | 10/1999 | Hunt | |
| 6,107,320 A | 8/2000 | Murugesan et al. | |
| 6,313,308 B1 | 11/2001 | Singh et al. | 548/235 |

FOREIGN PATENT DOCUMENTS

| | | |
|---|---|---|
| DE | 1059459 | 6/1959 |
| EP | 194548 | 9/1986 |
| EP | 443983 | 8/1991 |
| EP | 558258 | 9/1993 |
| EP | 569193 | 11/1993 |
| EP | 601386 | 6/1994 |
| EP | 633259 | 1/1995 |
| EP | 0 702 012 A | 3/1996 |
| EP | 725067 | 8/1996 |
| EP | 749964 | 12/1997 |
| GB | 897440 | 5/1962 |
| GB | 2228933 | 9/1990 |
| WO | 96/40681 | 12/1986 |
| WO | 93/10094 | 5/1993 |
| WO | 96/31492 | 10/1996 |
| WO | WO 97/29747 A | 8/1997 |
| WO | WO 97/29748 A | 8/1997 |
| WO | WO 98/33780 A | 8/1998 |
| WO | WO 01/44239 A2 | 6/2001 |

OTHER PUBLICATIONS

Chan et al., "Identification of a New Class of ETA Selective Endothelin Antagonists by Pharmacophore Direct Screening", Biochemical and Biophysical Research Communicatiosn, vol. 201, No. 1, May 30, 1994, 228–234.
Derwent Abstract No. 91–245550/35 Feb. 19, 1990.
CA 65: 2241d (1966).
Derwent Abstract No. 88–289069/41 Feb. 27, 1987.
Derwent Abstract No. 88–016295/09 Jul. 9, 1986.
Derwent Abstract No. 87–152485/22 Oct. 11, 1985.
Derwent Abstract No. 62299 E/30 Dec. 11, 1980.
Derwent Abstract No. 40927 D/23 Sep. 11, 1979.
Stein et al., The Discovery of Sulfonamide Endothelin Antagonists and the Development of the Orally Active ETA Antagonist 5–(Dimethylamino)–N–(3,4–dimethyl–5–isoxazoly)–1–naphthalenesulfonamide, J. Med. Chem., vol. 37, No. 3, Feb. 4, 1994, pp. 329–331.
Murugesan et al., "N–(heteroryl)..antagonists", CA 120:270370c, p. 1067 (1994).
Derwent Abstract No. 86–246709/38 Nov. 27, 1985.
Gmeiner, P. et al., Synthesis, p. 168–170, 1995.
Eric L. Williams, Tetrahedron Letters, vol. 33, No. 8, pp. 1033–1036, 1992.
M. Kertanto, Angew. Chem. internat. Edit., vol. 1, No. 8, p. 459, 1962.

*Primary Examiner*—Fiona T. Powers
(74) *Attorney, Agent, or Firm*—Deanna L. Baxam

(57) ABSTRACT

Methods for the preparation of biphenyl isoxazole sulfonamides and intermediates thereof. The present invention also relates to the novel intermediates prepared by these methods. The biphenyl isoxazole sulfonamides prepared by the present methods are endothelin antagonists useful, inter alia, for the treatment of hypertension.

13 Claims, No Drawings

METHODS FOR THE PREPARATION OF BIPHENYL ISOXAZOLE SULFONAMIDES

This application claims priority benefit under Title 35 §119(e) of U.S. Provisional Application No. 60/240,902 filed on Oct. 17, 2000, the entire contents of which are incorporated herein by reference.

FIELD OF THE INVENTION

The present invention relates to methods for the preparation of biphenyl isoxazole sulfonamides and intermediates thereof. The present invention also relates to the novel intermediates prepared by these methods. The biphenyl isoxazole sulfonamides prepared by the present methods are endothelin antagonists useful, inter alia, for the treatment of hypertension.

BRIEF DESCRIPTION OF THE INVENTION

The present methods allow preparation of biphenyl sulfonamides of the following formula I:

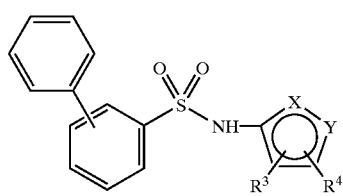

(I)

where the phenyl rings of the biphenyl group may independently be unsubstituted or substituted with one or more substituent groups, enantiomers and diastereomers, and salts, preferably pharmaceutically acceptable salts, thereof. Preferred substituent groups for the biphenyl group include those groups $R^{11}$ to $R^{14}$ described herein and especially, when the biphenyl group is a 2-biphenyl group, the group

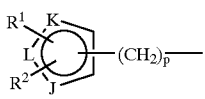

in the 4'-position. Preferred methods of the present invention allow preparation of compounds of the following formula Ia:

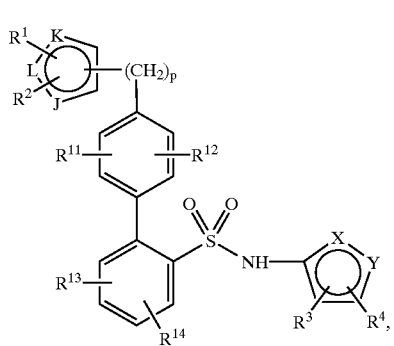

(Ia)

enantiomers and diastereomers, and salts, preferably pharmaceutically acceptable salts, thereof. Throughout this specification, the above symbols are defined as follows:
one of X and Y is N and the other is O;
$R^1$, $R^2$, $R^3$ and $R^4$ are each directly bonded to a ring carbon and are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)R$^5$;
  (h) —CO$_2$H or —CO$_2$R$^5$;
  (i) —Z$^4$—NR$^6$R$^7$;
  (j) —Z$^4$—N(R$^{10}$)—Z$^5$—NR$^8$R$^9$; or
  (k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;
$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;
$R^6$, $R^7$, $R^8$, $R^9$ and $R^{10}$ are each independently
  (a) hydrogen; or
  (b) alkyl, cycloalkyl, cycloalkylalkyl, cycloalkenylalkyl, aryl or aralkyl, any of which may be substituted with $Z^1$, $Z^2$ and $Z^3$; or
$R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;
$R^{11}$, $R^{12}$, $R^{13}$ and $R^{14}$ are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) heterocycle, substituted heterocycle or heterocyclooxy;
  (d) halo;
  (e) hydroxyl;
  (f) cyano;
  (g) nitro;
  (h) —C(O)H or —C(O)R$^5$;
  (i) —CO$_2$H or —CO$_2$R$^5$;
  (j) —SH, —S(O)$_n$R$^5$, —S(O)$_m$—OH, —S(O)$_m$—OR$^5$, —O—S(O)$_m$—OR$^5$, —O—S(O)$_m$OH or —O—S(O)$_m$—R$^5$;
  (k) —Z$^4$—NR$^6$R$^7$; or
  (l) —Z$^4$—N(R$^{10}$)—Z$^5$—NR$^8$R$^9$;
$Z^1$, $Z^2$ and $Z^3$ are each independently
  (a) hydrogen;
  (b) halo;
  (c) hydroxy;
  (d) alkyl;
  (e) alkenyl;
  (f) aryl;
  (g) aralkyl;
  (h) alkoxy;
  (i) aryloxy;
  (j) aryloxy;

(k) heterocycle, substituted heterocycle or heterocyclooxy;
(l) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
(m) oxo;
(n) nitro;
(o) cyano;
(p) —C(O)H or —C(O)Z$^6$;
(q) —CO$_2$H or —CO$_2$Z$^6$;
(r) —Z$^4$—NZ$^7$Z$^8$;
(s) —Z$^4$—N(Z$^{11}$)—Z$^5$—H;
(t) —Z$^4$—N(Z$^{11}$)—Z$^5$—Z$^6$; or
(u) —Z$^4$—N(Z$^{11}$)—Z$^5$—NZ$^7$Z$^8$;

Z$^4$ and Z$^5$ are each independently
(a) a single bond;
(b) —Z$^9$—S(O)$_n$—Z$^{10}$—;
(c) —Z$^9$—C(O)—Z$^{10}$—;
(d) —Z$^9$—C(S)—Z$^{10}$—;
(e) —Z$^9$—O—Z$^{10}$—;
(f) —Z$^9$—S—Z$^{10}$—;
(g) —Z$^9$—O—C(O)—Z$^{10}$—; or
(h) —Z$^9$—C(O)—O—Z$^{10}$—;

Z$^6$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy and trihaloalkoxy; or heterocycle or substituted heterocycle;

Z$^7$ and Z$^8$ are each independently hydrogen, alkyl, cycloalkyl, cycloalkylalkyl, cycloalkenylalkyl, aryl or aralkyl, or Z$^7$ and Z$^8$ together are alkylene or alkenylene, completing a 3- to 8-membered saturated or unsaturated ring together with the nitrogen atom to which they are attached;

Z$^9$ and Z$^{10}$ are each independently a single bond, alkylene, alkenylene or alkynylene;

z$^{11}$ is
(a) hydrogen; or
(b) alkyl, alkyl substituted with one, two or three halogens, cycloalkyl, cycloalkylalkyl, cycloalkenylalkyl, aryl or aralkyl;
or any two of Z$^7$, Z$^8$ and Z$^{11}$ together are alkylene or alkenylene, completing a 3- to 8-membered saturated or unsaturated ring together with the atoms to which they are attached;

J is O, S, N or NR$^{15}$;
K and L are N or C, provided that at least one of K or L is C;
R$^{15}$ is hydrogen, alkyl, hydroxyethoxy methyl or methoxyethoxy methyl;
each m is independently 1 or 2;
each n is independently 0, 1 or 2; and
p is 0 or an integer from 1 to 2.

In accordance herewith, a compound of the formula I or salt thereof may be prepared by a method comprising the steps of:
(a) contacting a pinacol ester of the formula II or salt thereof:

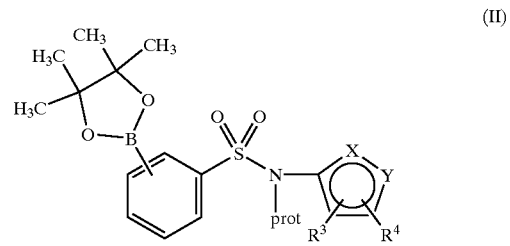

where the phenyl ring of said formula II may be further substituted, such as with one or more groups described for the groups R$^{11}$ to R$^{14}$ herein, with a compound of the formula III or salt thereof:

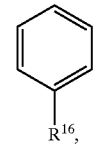

where R$^{16}$ is halogen or a group —O—Q, where Q is —SO$_2$CF$_3$, —SO$_2$CH$_3$, or

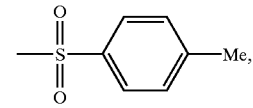

and where the phenyl ring of said formula III may be further substituted, such as with one or more groups described for the groups R$^{11}$ to R$^{14}$ herein, and especially, when the biphenyl group of said compound of the formula I or salt thereof is a 2-biphenyl, the group

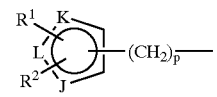

para to the halo group, in the presence of a palladium(0) catalyst and, preferably, a base, to form a nitrogen-protected compound of the formula IV or salt thereof:

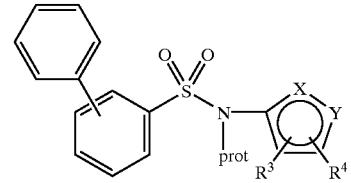

where the phenyl rings of the biphenyl group may independently be unsubstituted or substituted with one or more substituent groups; and (b) deprotecting the nitrogen of said compound of the formula IV or salt thereof to form said compound of the formula I or salt thereof.

"Prot", as used in formula II and throughout this specification, denotes an alkoxymethyl nitrogen-protecting group, and is preferably methoxymethyl ("MOM").

In a preferred embodiment, a compound of the formula Ia or salt thereof may be prepared by a method comprising the steps of:

(a) contacting a pinacol ester of the formula IIa or salt thereof:

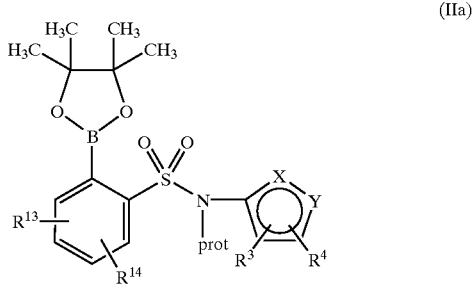

(IIa)

with a compound of the formula IIIa or salt thereof:

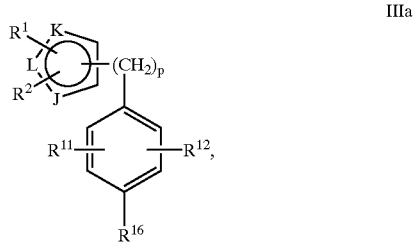

IIIa where $R^{16}$ is preferably halo (preferably chloro, bromo or iodo and most preferably bromo or iodo), in the presence of a palladium(0) catalyst and, preferably, a base, to form a nitrogen-protected compound of the formula IVa or salt thereof:

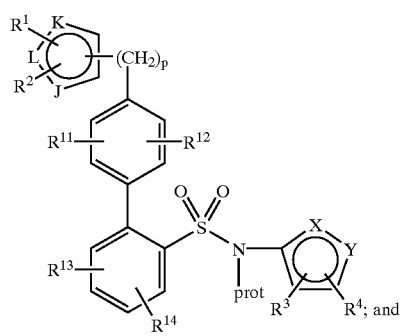

(IVa)

(b) deprotecting the nitrogen of said formula IVa compound or salt thereof to form said compound of the formula Ia or salt thereof.

The present methods for preparing a compound of the formula I or salt thereof are advantageous in that they provide high yields with minimal or no formation of impurities. The present methods are further advantageous in that they provide a superior route to compounds of formula I in terms of practicality, ease of operation, cost and safety.

Further provided herewith are novel intermediates of the present methods, and novel methods for preparing such intermediates.

DETAILED DESCRIPTION OF THE INVENTION

The present invention is described further as follows. Listed below are definitions of terms used in this specification. These definitions apply to the terms as used throughout this specification, individually or as part of another group, unless otherwise indicated in specific instances.

The term "alkyl" or "alk-" refers to straight or branched chain hydrocarbon groups having 1 to 10 carbon atoms, preferably 1 to 7 carbon atoms. The expression "lower alkyl", refers to alkyl groups of 1 to 4 carbon atoms.

The term "alkoxy" refers to alkyl-O—.

The term "aryl" or "ar-" refers to phenyl, naphthyl and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., —$(CH_2)_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —$CH_2$—CH=CH—, —$CH_2$—CH=CH—$CH_2$—, —$C(CH_3)_2$CH=CH— and —CH$(C_2H_5)$—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —$CH_2$—C≡C—, —CH($CH_3$)—C≡C— and —C≡C—CH($C_2H_5$)$CH_2$—.

The term "alkanoyl" refers to groups of the formula —C(O) alkyl.

The terms "cycloalkyl" and "cycloalkenyl" refer to cyclic hydrocarbon groups of 3 to 8 carbon atoms.

The term "hydroxyalkyl" refers to an alkyl group including one or more hydroxy radicals such as —$CH_2CH_2OH$, —$CH_2CH_2OHCH_2OH$, —CH($CH_2OH$)$_2$ and the like.

The terms "halogen" and "halo" refer to fluorine, chlorine, bromine and iodine.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms or sulfur atoms, where the nitrogen and sulfur heteroatoms may optionally be oxidized and the nitrogen heteroatoms may optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

The expression "substituted heterocycle" refers to a heterocycle substituted with 1, 2 or 3 of the following:

(a) alkyl, especially lower alkyl;
(b) hydroxy (or protected hydroxy);
(c) halo;
(d) oxo (i.e. =O);
(e) amino, alkylamino or dialkylamino;
(f) alkoxy;
(g) carbocyclo, such as cycloalkyl;
(h) carboxy;
(i) heterocyclooxy;
(j) alkoxycarbonyl, such as unsubstituted lower alkoxycarbonyl;
(k) carbamyl, alkylcarbamyl or dialkylcarbamyl;
(l) mercapto;
(m) nitro;
(n) cyano;
(o) carboalkoxy;
(p) sulfonamido, sulfonamidoalkyl or sulfonamidodialkyl;
(q)

(r)

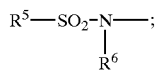

(s) aryl;
(t) alkylcarbonyloxy;
(u) arylcarbonyloxy;
(v) arylthio;
(w) aryloxy;
(x) alkylthio;
(y) formyl;
(z) arylalkyl; or
(a') aryl substituted with alkyl, cycloalkyl, alkoxy, hydroxy, amino, alkylamino, dialkylamino, halo or trihaloalkyl.

The term "heterocyclooxy" denotes a heterocyclic group bonded through an oxygen bridge.

Throughout the specification, groups and substituents thereof may be chosen to provide stable moieties and compounds.

The compounds of formula I and intermediates thereof may form salts which are also within the scope of this invention. Pharmaceutically acceptable (i.e., non-toxic, physiologically acceptable) salts are preferred, although other salts are also useful, for example, in isolating or purifying the compounds of this invention.

The compounds of formula I and intermediates thereof may form salts with alkali metals such as sodium, potassium and lithium, with alkaline earth metals such as calcium and magnesium, with organic bases such as dicyclohexylamine, t-butyl amine, benzathine, N-methyl-D-glucamide and hydrabamine, and with amino acids such as arginine, lysine and the like. Such salts may be obtained by reacting these compounds with the desired ion in a medium in which the salt precipitates or in an aqueous medium followed by lyophilization.

When groups such as the $R^1$ to $R^4$ or $R^{11}$ to $R^{14}$ substituents comprise a basic moiety, such as amino or substituted amino, the compounds of formula I and intermediates thereof may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate and various other sulfonates, nitrates, phosphates, borates, acetates, tartrates, maleates, citrates, succinates, benzoates, ascorbates, salicylates and the like. Such salts may be formed by reacting these compounds in an equivalent amount of the acid in a medium in which the salt precipitates or in an aqueous medium followed by lyophilization.

In addition, when groups such as the $R^1$ to $R^4$ or $R^{11}$ to $R^{14}$ substituents comprise a basic moiety such as amino, zwitterions ("inner salts") may be formed.

Certain groups such as the $R^1$ to $R^4$ and $R^{11}$ to $R^{14}$ substituents of the compounds of the invention may contain asymmetric carbon atoms. The compounds of the invention such as those of the formula I and salts thereof may exist, therefore, in enantiomeric and diastereomeric forms and in racemic mixtures thereof. All are within the scope of this invention. Additionally, compounds such as those of formula I and salts thereof may exist as enantiomers even in the absence of asymmetric carbons (e.g., atropisomers). All such enantiomers are within the scope of this invention.

U.S. Pat. No. 5,612,359, U.S. Pat. No. 5,827,869, U.S. Pat. No. 5,846,990, U.S. Pat. No. 5,856,507, U.S. Pat. No. 6,043,265 and U.S. patent application Ser. No. 09/528,819, filed Mar. 20, 2000 by Singh et al. entitled "Methods for the Preparation of Biphenyl Isoxazole Sulfonamides", describing endothelin antagonists, starting materials and methods, are each incorporated herein by reference in their entirety.

Coupling of Formulae II and III Compounds, and Deprotection

A compound of the formula I or salt thereof may be prepared by coupling a pinacol ester of the formula II or salt thereof with a compound of the formula III or salt thereof, and by deprotecting the nitrogen-protected compound IV or salt thereof formed by the aforementioned coupling.

Coupling of compounds of the formulae II and III or salts thereof is conducted in the presence of a palladium(0) catalyst, preferably palladium acetate/triphenylphosphine or other palladium (II) salt/triphenylphosphine, tetrakistri phenylphosphine palladium or tris(dibenzylideneacetone) dipalladium, and, preferably, a base, preferably aqueous potassium carbonate or sodium carbonate, to form a nitrogen-protected compound of the formula IV or salt thereof. The preferred molar ratio of palladium (II) salt to triphenylphosphine is between 1:1 and 1:3. See the conditions for catalysis described by A. Suzuki et al., *Pure & Applied Chemistry*, 63, 419–422 (1991); A. Martin et al., *Acta. Chem. Scand.*, 47, 221 (1993); H. Jendralla et al., *Liebig Ann.*, 1253 (1995), G. B. Smith et al., *J. Org. Chem.*, 1994, 59, 8151 all incorporated herein by reference.

When the compound III is a compound IIIa, protection of the heteroatoms J and K or L may be desirable, in certain instances, to facilitate the coupling reaction. For example, when J and K or L are N, one of the groups may be protected by a suitable protecting group such as t-butoxycarbonyl, etc. Specific $R^{11}$–$R^{14}$ groups may be chosen to be compatible with the reaction conditions. Additionally, specific $R^{11}$–$R^{14}$ groups may be converted into alternative $R^1$–$R^{14}$ groups, either before or after coupling, using any suitable methods such as those known in the art.

The coupling method is preferably conducted at a temperature of from about 25° C. to about 100° C. (most preferably from about 45° C. to about 75° C.), at a pressure of about 1 atm, and under an atmosphere of argon or nitrogen. Molar ratios of the pinacol ester II or salt thereof to the compound III or salt thereof are preferably from about 1:1 to about 1:1.2. Amounts of palladium(0) catalyst and base are selected to catalyze the coupling reaction and are preferably from about 2.5 mol % to about 10 mol %, and from about 2.5 equivalents to about 7 equivalents, respectively. Solvents are preferably employed which are selected from aqueous or organic liquids such as acetone, ethanol, toluene, tetrahydrofuran, dimethoxyethane and water, or mixtures thereof, preferably a mixture of toluene, ethanol and water. Amounts of solvent are preferably those wherein the pinacol ester II or salt thereof is from about 4 to about 9% by weight, based on the combined weight of solvent and pinacol ester II or salt thereof. For example, the following are exemplary ranges for solvent/pinacol ester II/base: tetrahydrofuran (30 to 70 mL), toluene (200 to 300 mL), ethanol (80 to 160 mL)/pinacol ester II (15 to 20 g)/aqueous 2M sodium carbonate (100 to 150 mL).

Residual palladium catalyst is preferably removed, either before or after deprotection of the compound of formula IV or salt thereof, by contact with a chelating agent such as trithiocyanuric acid ("TMT"). Crystallization providing a suitable crystalline form of the compound of the formula I or salt thereof, subsequent to deprotection of the compound of the formula IV or salt thereof, is also contemplated by the present invention. Preferably, crystallization is achieved from a supersaturated isopropanol solution, with or without the presence of co-solvents such as heptane or water, especially where seeded with the desired crystalline form. Most preferably, crystallization is conducted by the methods of the Examples herein.

Compounds of the formula III and salts thereof may be prepared by methods analogous to those described in U.S. Pat. No. 5,612,359, U.S. Pat. No. 5,827,869, U.S. Pat. No. 5,846,990, U.S. Pat. No. 5,856,507, U.S. Pat. No. 6,043,265 and U.S. patent application Ser. No. 09/528,819. Preferably, oxazole compounds of the formula IIIa or salts thereof are prepared by the novel methods for their preparation described herein. Compounds of the formula II and salts thereof are preferably prepared by the novel methods for their preparation described herein.

Deprotection of the formula IV compound or salt thereof formed by the present coupling method may be conducted by any suitable method, such as methods analogous to those described in U.S. Pat. No. 5,612,359, U.S. Pat. No. 5,827,869, U.S. Pat. No. 5,846,990, U.S. Pat. No. 5,856,507, U.S. Pat. No. 6,043,265 and U.S. patent application Ser. No. 09/528,819. Preferably, deprotection is conducted by heating in a mixture of aqueous HCl and ethanol.

Preparation of Formula II Compounds

The pinacol esters of the formula II and salts thereof may themselves be formed by novel methods provided herein. In accordance herewith, a pinacol ester of the formula II or salt thereof may be prepared by a method comprising the steps of:

(a) contacting a compound of the formula V or salt thereof:

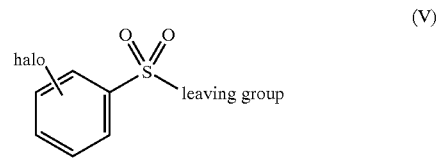

(V)

where the phenyl group of said formula V may be further substituted, such as with one or more groups described for the groups $R^{11}$ to $R^{14}$ herein, and where halo is preferably bromo, chloro or iodo, most preferably bromo, with an amine of the formula VI or salt thereof:

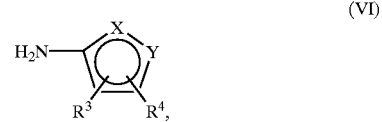

(VI)

in the presence of an organic base (e.g. pyridine) (preferably in the presence of a catalyst such as DMAP) and optionally an organic solvent, to form a compound of the formula VII or salt thereof:

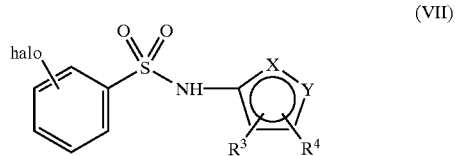

(VII)

where the phenyl group of said formula VII may be further substituted, such as with one or more groups described for the groups $R^{11}$ to $R^{14}$ herein;

(b) protecting the nitrogen of said compound of the formula VII or salt thereof by contacting the compound of formula VII with a compound of formula XX

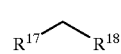

XX where $R^{17}$ is alkoxy (preferably methoxy), or halogen, and $R^{18}$ is alkoxy (preferably methoxy), in the presence of a Lewis or protic acid (preferably $P_2O_5$) when $R^{17}$ is alkoxy, or in the presence of a base when $R^{17}$ is halo, to form a compound of the formula VIII or salt thereof:

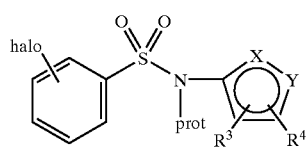

(VIII)

where the phenyl group of said formula VIII may be further substituted, such as with one or more groups described for the groups $R^{11}$ to $R^{14}$ herein;

(c) lithiating said compound of the formula VIII or salt thereof with an alkyl or aryl lithium compound and contacting the lithiated product formed with a trialkylborate, followed by hydrolysis, to form a boronic acid of the formula IX or salt thereof:

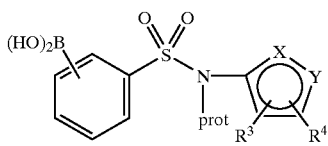

(IX)

where the phenyl group of said formula IX may be further substituted, such as with one or more groups described for the groups $R^{11}$ to $R^{14}$ herein; and (d) contacting said compound of the formula IX or salt thereof with pinacol (i.e., 2,3-dimethyl-2,3-butanediol), with removal of water, thereby forming said compound of the formula II or salt thereof.

In a preferred embodiment, a pinacol ester of the formula IIa or salt thereof may be prepared by a method comprising the steps of:

(a) contacting a compound of the formula Va or salt thereof:

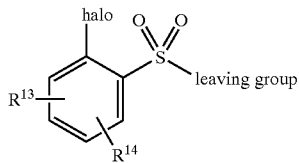

(Va)

with an amine of the formula VIa or salt thereof:

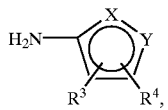

(VIa)

in the presence of an organic base and optionally and organic solvent, to form a compound of the formula VIIa or salt thereof:

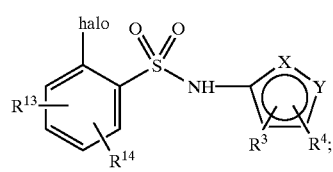

(VIIa)

(b) protecting the nitrogen of said compound of the formula VIIa or salt thereof by contacting the compound of formula VII with a compound of formula XX

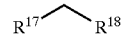

XX where $R^{17}$ and $R^{18}$ are each methoxy, in the presence of a Lewis or protic acid (preferably $P_2O_5$) to form a compound of the formula VIIIa or salt thereof:

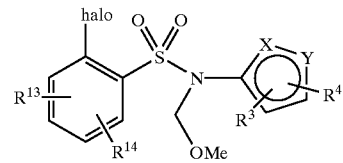

VIIIa (c) lithiating said compound of the formula VIIIa or salt thereof with an alkyl or aryl lithium compound and contacting the lithiated product formed with a trialkylborate, followed by hydrolysis, to form a boronic acid of the formula IXa or salt thereof:

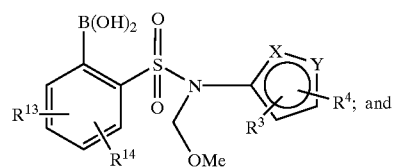

IXa (d) contacting said compound of the formula IXa or salt thereof with pinacol, with removal of water, thereby forming said compound of the formula IIa or salt thereof.

The term "leaving group", as used herein, denotes any suitable leaving group such as a halo group, preferably chloro. Any suitable organic base may be employed in step (a). Preferred organic bases include amines such as pyridine or a trialkylamine. The organic solvent optionally employed in step (a) is preferably a haloalkane, such as dichloromethane or 1,2-dichloroethane, or the organic base, such as neat pyridine, may also function as the solvent.

As described above, compounds of the formula VIII and salts thereof may be prepared by contacting a compound of the formula V or salt thereof with an amine compound of the formula VI or salt thereof, and by protecting the nitrogen of the product compound VII or salt thereof. The formula VIII compound or salt thereof obtained is then lithiated with an alkyl or aryl lithium compound, preferably with n-butyl lithium or phenyl lithium, at temperatures which are preferably from about −40° C. to about −105° C. (especially, from about −70° C. to about −100° C.), to form the compound:

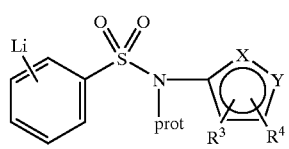

where the phenyl group of said compound may be further substituted, such as with one or more groups described for the groups $R^{11}$ to $R^{14}$ herein, or salt thereof, preferably the compound:

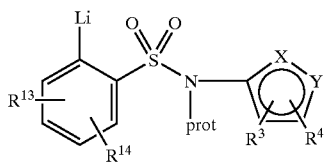

or salt thereof. Treatment of the lithiated compound or salt thereof with a trialkylborate such as triisopropylborate or, preferably, trimethylborate, at temperatures which are preferably from about −40° C. to about −105° C. (especially, from about −70° C. to about −100° C.), provides the following boronate ester:

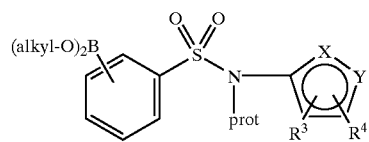

where the phenyl group of said compound may be further substituted, such as with one or more groups described for the groups $R^{11}$ to $R^{14}$ herein, or salt thereof, preferably the boronate ester:

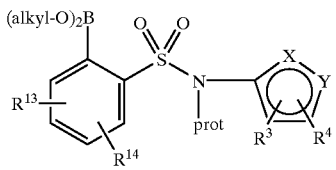

or salt thereof, which may then be hydrolyzed with a suitable acid, preferably an aqueous acid such as aqueous hydrochloric acid, or with a suitable base, to form the boronic acid IX or salt thereof. The hydrolysis step, forming the boronic acid IX or salt thereof, is advantageous as the boronic acid provides a handle for purification (the boronic acid moiety) by simple physical/chemical means whereas the the boronate ester from which it is obtained does not. The aforementioned steps may be conducted by methods analogous to those described in, and with starting materials of the formulae V and VI and salts thereof prepared by methods analogous to those described in U.S. Pat. No. 5,612,359, U.S. Pat. No. 5,827,869, U.S. Pat. No. 5,846,990, U.S. Pat. No. 5,856,507, U.S. Pat. No. 6,043,265 and U.S. patent application Ser. No. 09/528,819.

The boronic acid IX or salt thereof may then be contacted with pinacol, with the removal of water, to form the corresponding pinacol ester II or salt thereof. Removal of water may be conducted, for example, by the addition of a drying agent such as magnesium sulfate or by azeotropic removal of water by heating with a solvent such as toluene. This reaction is preferably conducted at a temperature of from about 110° C. to about 120° C. (most preferably from about 112° C. to about 115° C.), at a pressure of about 1 atm, and under an atmosphere of argon or nitrogen. Molar ratios of pinacol to the boronic acid IX or salt thereof are preferably from about 1:1 to about 1.1:1. Solvents are preferably employed which are selected from organic liquids such as toluene. Amounts of solvent are preferably those wherein the boronic acid IX or salt thereof is from about 4 to about 10% by weight, based on the combined weight of solvent and boronic acid IX or salt thereof.

The boronic acid IX or salt thereof (preferably, the preferred boronic acid IXa or salt thereof) may be directly coupled with the compound III or salt thereof to form a formula IV compound or salt thereof. This method, especially where the compound III or salt thereof is a halophenyl compound or salt thereof (preferably, an iodophenyl or bromophenyl compound IIIa or salt thereof), is also contemplated by the present invention. The pinacol ester II or salt thereof in place of the boronic acid IX or salt thereof may be advantageous, however, as the pinacol ester compounds are highly stable, and lesser amounts of impurities may be formed and higher yields of the formula IV compound or salt thereof may be obtained upon coupling with a halophenyl compound III or salt thereof.

Preparation of Formula III Compounds

Compounds of the formula III and salts thereof may be prepared by methods analogous to those described in U.S. Pat. No. 5,612,359, U.S. Pat. No. 5,827,869, U.S. Pat. No. 5,846,990, U.S. Pat. No. 5,856,507, U.S. Pat. No. 6,043,265 and U.S. patent application Ser. No. 09/528,819. Preferred compounds of the formula IIIa and salts thereof bearing an oxazole ring may also be formed by novel methods provided herein. In accordance herewith, a formula IIIa(1) oxazole or salt thereof may be prepared by a method comprising the steps of:

(a) contacting a phenyl acid halide X or salt thereof:

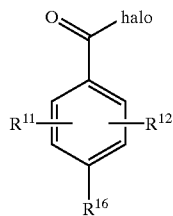

with either triazole in the presence of a base (preferably sodium hydride), or an N-trimethylsilyl derivative of triazole, to form a triazole amide the formula XI or salt thereof:

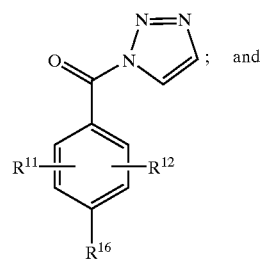

(b) effecting a nitrogen elimination rearrangement (e.g., thermally, photochemically, or by other catalytic means known in the art) of the triazole amide of formula XI or salt thereof, to form an oxazole of the formula IIIa(1) or salt thereof:

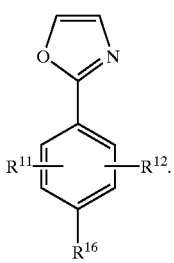

IIIa(1)

The starting phenyl acid halide of formula X or salt thereof is commercially available or may readily be prepared by one of ordinary skill in the art. The halo group of the acid halide moiety is preferably chloro; $R^{16}$ is preferably bromo, chloro, or iodo, most preferably iodo or bromo. Triazole and its N-trimethylsilyl derivatives are also commercially available or may readily be prepared by one of ordinary skill in the art.

The base employed in step (a) may be any suitable base, and is preferably sodium hydride. Coupling of the acid halide of formula X or salt thereof with 1,2,3-triazole and subsequent nitrogen elimination/rearrangement is conducted in a solvent such as sulfolane in the presence of potassium carbonate at temperatures of 80–110° C. or by preforming the salt of 1,2,3-triazole with a base such as sodium hydride in a solvent such as sulfolane, and reacting the salt with the acid chloride X at temperatures of 80–110° C. Coupling of the acid halide of formula X with N-trimethylsilyl-1,2,3-triazole and subsequent nitrogen elimination/rearrangement can be effected in solvents like toluene, xylenes, and sulfolane at temperatures of 80–150° C.

Preferred compounds of the formula I can be prepared from compounds of the formula IIIa(2)

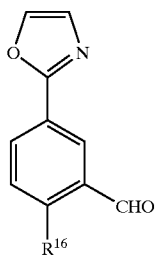

IIIa(2)

which may also be formed by novel methods provided herein. In accordance herewith a compound of formula IIIa(2) may be prepared by a method comprising the step of:

(a) hydrolyzing a compound of formula IIIb or salt thereof

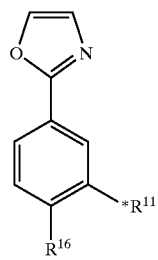

IIIb where $*R^{11}$ is dihalomethyl (preferably dibromomethyl,
in the presence of a nucleophilic base (e.g. a secondary amine such as morpholine) to form a compound of formula IIIa(2).

Compounds of the formula IIIb may be formed from a process comprising the steps of:

(a) contacting a compound of formula XXI

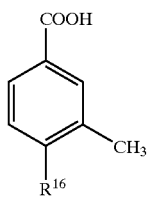

XXI with a suitable halogenating agent (such as N-bromosuccinimide or 1,3-dibromo-5,5-dimethyl hydantoin to form a compound of the formula XXII

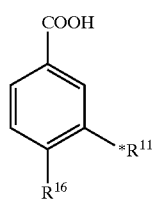

XXII where $*R^{11}$ is dihalomethyl (preferably dibromomethyl);

(b) converting said compound of formula XXII to an aryl acid halide compound of formula Xa

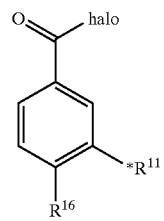

Xa (e.g. by reacting XXII with reagants such as oxalylchloride, thionyl chloride, phosphorus trichloride, phosphorus pentachloride or phosphorus tribromide; and (c) converting said compound of formula Xa to a compound of formula IIIb (e.g., through reaction with triazole or an N-trimethylsilyl derivative thereof as described previously herein, or through other methods such as those described in U.S. Pat. No. 5,612,359, U.S. Pat. No. 5,827,869, U.S. Pat. No. 5,846,990, U.S. Pat. No. 5,856,507, U.S. Pat. No. 6,043,265 and U.S. patent application Ser. No. 09/528,819.

The compound XXI can be reacted with a brominating agent such as N-bromosuccinimide at temperatures of 100–120° C. in solvents such as trifluorotoluene or dichlorobenzene in the presence of radical initiators such 2,2'-azo-bis-isobutyronitrile to provide XXII. Conversion of XXII to acid chloride Xa can be carried out with oxalyl chloride in toluene or dichloromethane in the presence of a small amount of N,N-dimethyl formamide. Coupling of the acid halide of formula Xa with 1,2,3-triazole and subsequent nitrogen elimination/rearrangement is conducted in a solvent such as sulfolane in the presence of potassium carbonate at temperatures of 80–110° C. or by preforming the salt of 1,2,3-triazole with a base such as sodium hydride in sulfolane, and reacting the salt with the acid chloride Xa at temperatures of 80–110° C. The compounds of the formula IIIa and salts thereof may also be used in a further method ("reverse coupling") contemplated by the present invention, for the preparation of compounds of the formula Ia or salts thereof, comprising the steps of:

(a) lithiating a compound of the formula IIIa or salt thereof:

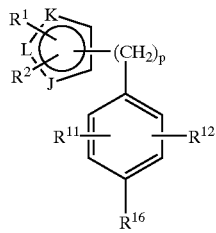

IIIa preferably, a compound of the formula IIIa(1) or salt thereof, with an alkyl or aryl lithium compound in the presence of a trialkylborate, followed by hydrolysis, to form a boronic acid of the formula XIII or salt thereof:

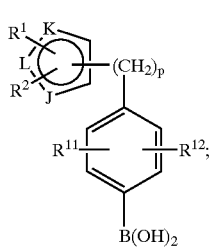

(XIII)

(b) contacting the boronic acid of the formula XIII or salt thereof with a compound of the formula VIIIa or salt thereof:

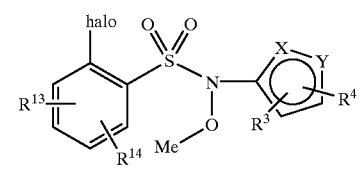

VIIIa where halo is preferably bromo, iodo or chloro, most preferably bromo, in the presence of a palladium(0) catalyst and, preferably, a base, to form a nitrogen-protected compound of the formula IVa or salt thereof:

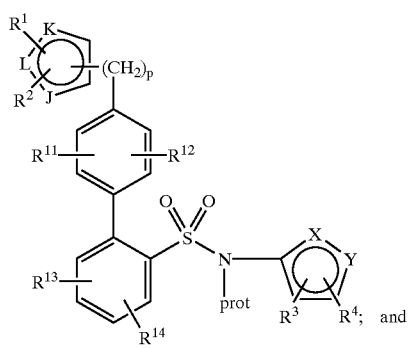

(IVa)

(c) deprotecting the nitrogen of said formula IVa compound or salt thereof to form said compound of the formula Ia or salt thereof.

With respect to this method, lithiation is conducted in the presence of a trialkylborate, followed by hydrolysis which may be conducted under conditions as described herein for the preparation of boronic acids of the formula IX and salts thereof. Coupling in the presence of a palladium(0) catalyst and, preferably, base, and deprotection of the nitrogen-protected coupled product, may be conducted under conditions as described herein for the coupling of compounds of the formulae II and III and salts thereof, and deprotection of the product thereof. Lithiation provides a compound having the following structure or a salt thereof:

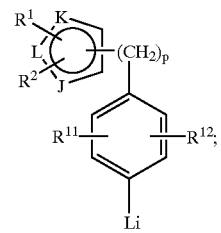

contact with a trialkylborate provides the following boronate ester or a salt thereof:

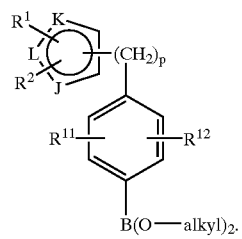

Preferred Compounds

It is preferred that the compounds employed in or prepared by the present methods contain one or more, preferably all where appropriate, of the following substituents:

X is O and N is Y;

the ring bearing K, L and J is 2-oxazole;

p is zero;

$R^1$ and $R^2$ are each independently hydrogen, alkyl, alkoxy, aryl, hydroxyalkyl, —$CO_2R^5$ or —$Z^4$—$NR^6R^7$, most preferably lower alkyl or hydrogen;

$R^3$ and $R^4$ are each independently alkyl, most preferably lower alkyl, especially methyl; and $R^{11}$, $R^{12}$, $R^{13}$ and $R^{14}$ are each independently hydrogen, hydroxy, amino, heterocyclo, alkenyl, alkoxy, carboxamide or substituted lower alkyl, most preferably, $R^{12}$ to $R^{14}$ are hydrogen and $R^{11}$ is hydrogen, hydroxy, amino, heterocyclo, alkenyl, alkoxy, carboxamide or substituted lower alkyl (such as —$CH_2$—$N(CH_3)$—$C(O)$—$CH_2$—$C(CH_3)_3$).

Compounds of the formula I of particular interest include N-(3,4-dimethyl-5-isoxazolyl)-4'-(2-oxazolyl)-[1,1'-biphenyl]-2-sulfonamide and salts thereof, and N-[[2'-[[(4,5-dimethyl-3-isoxazolyl)amino]sulfonyl]-4-(2-oxazolyl)[[1,1'-biphenyl]-2-yl]methyl]-N,3,3-trimethylbutanamide and salts thereof.

Utility of Compounds of Formula I and Salts Thereof as Endothelin Antagonists

The compounds of the formula I and salts thereof are antagonists of ET-1, ET-2 and/or ET-3 and are useful in treatment of conditions associated with increased ET levels (e.g., dialysis, trauma and surgery) and of all endothelin-dependent disorders. They are thus useful as antihypertensive agents. By the administration of a composition having one (or a combination) of the compounds of this invention, the blood pressure of a hypertensive mammalian (e.g., human) host is reduced. They are also useful in pregnancy-induced hypertension and coma (preeclampsia and eclampsia), acute portal hypertension and hypertension secondary to treatment with erythropoietin.

The compounds of the present invention are also useful in the treatment of disorders related to renal, glomerular and mesangial cell function, including acute and chronic renal failure, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention may also be useful in the treatment of disorders related to paracrine and endocrine function.

The compounds of the present invention are also useful in the treatment of endotoxemia or endotoxin shock as well as hemorrhagic shock.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention may also be useful as anti-arrhythmic agents; anti-anginal agents; anti-fibrillatory agents; anti-asthmatic agents; anti-atherosclerotic and anti-arteriosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease and Takayashul's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatotoxicity and sudden death. The compounds of this invention may be useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention may be useful in therapy for metabolic and neurological disorders; cancer; insulin-dependent and non insulin-dependent diabetes mellitus; neuropathy; retinopathy; maternal respiratory distress syndrome; dysmenorrhea; epilepsy; hemorrhagic and ischemic stroke; bone remodeling; psoriasis; and chronic inflammatory diseases such as rheumatoid arthritis, osteoarthritis, sarcoidosis and eczematous dermatitis (all types of dermatitis).

The compounds of the formula I and salts thereof can also be formulated in combination with endothelin converting enzyme (ECE) inhibitors, such as phosphoramidon; thromboxane receptor antagonists; potassium channel openers; thrombin inhibitors (e.g., hirudin and the like); growth factor inhibitors such as modulators of PDGF activity; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; dual NEP-ACE inhibitors; HMG CoA reductase inhibitors such as pravastatin and mevacor; squalene synthetase inhibitors; bile acid sequestrants such as questran; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The present invention will now be further described by the following working examples, which illustrate preferred embodiments of the invention.

EXAMPLE 1

Preparation of Pinacol Ester Compound II

A. N-(4,5-Dimethylisoxazol-3-yl)-2-bromobenzenesulfonamide

A 500 mL flask was charged with 2-bromobenzene sulfonyl chloride (153.3 g) and dimethylaminopyridine (7.37 g, 0.1 equiv), purged with argon and cooled in an ice-brine bath. Pyridine (300 mL) was added, and the mixture stirred. A separate flask containing 3-amino-4,5-dimethyl isoxazole, (73.95 g) in anhydrous pyridine[3] (300 mL) under argon was cooled in an ice bath. When the internal temperature of the pyridine-bromobenzenesulfonyl chloride solution was ~−3° C., the isoxazole-pyridine solution was added dropwise by cannula. The addition required ~90 min. Quantitative transfer of the isoxazole was achieved with a 10 mL pyridine rinse. Upon completion of addition, the ice was removed from the brine-ice bath, and the internal temperature of the reaction vessel warmed to approximately 8–10° C. over 1 h. The reaction vessel was then immersed in a preheated oil bath at 42° C. and maintained at this temperature for 24.5 h. The warm solution was cannulated dropwise into ice cold 6N HCl (8 L) with vigorous stirring over approximately 90 min. Immediate precipitation occurred. The mixture was stirred in the ice-water bath for approximately 1 h, and the yellow solid collected by suction filtration on a medium porosity glass frit. The filter cake was washed with cold deionized water (4×0.5 L), taking care to mix the filter cake with each wash. The solid was air suction dried for 24 h affording a yellow powder: 185.5 g, 93.4%, HPLC area percent 97.7. The solid was dissolved in ethyl acetate (3.7 L or 20 mL/g), charcoal (46.1 g, Darco KB, lot 1F-074) added, the mixture heated briefly to 58° C., cooled to RT and stirred for 12 h, filtered through celite, the celite pad rinsed with ethyl acetate (5×200 mL) and evaporated to dryness.

The solid was dissolved in ethyl acetate (~500 mL), and stirred in an oil bath at ~63–68° C. Warm hexanes (750 mL) were added (rapidly at first, then dropwise after crystallization commenced).

Precipitation/crystallization began when ~100 mL of hexanes had been added. Upon completion of addition, the oil bath was removed and after ~2 h stirring was stopped. The mixture cooled to RT overnight (13 h) then at ~5° C. for 32 h, collected and washed with ice cold 1:2 ethyl acetate:hexanes (~100 mL). After drying for 15 h the white solid weighed 160.3 g, 81% overall yield, HPLC AP[7] 99.5, mp 143–145 degrees. The infra-red and $^1$H NMR spectra were consistent with the assigned structure. Mass spectrum: m/e 331 (MH$^+$); Elemental Analysis: for $C_{11}H_{11}BrN_2O_3S$: C; Calc. 39.89, Found: 39.86; H; Calc. 3.35, Found: 3.28; N; Calc. 8.46, Found: 8.47.

B. 1-Bromo-N-(methoxymethyl)-N-(4,5-dimethyl-3-isoxazolyl)benzenesulfonamide

A dry 1 L round bottom flask was charged with BMS-224339 (26.5 g, 80 mmol), celite (52.8 g), dichloromethane (400 mL), dimethoxymethane (56 mL) and $P_4O_{10}$ (10 g). The mixture was immersed in a pre-heated oil bath at 38° C. and stirred for 13 h. HPLC analysis of an aliquot indicated the reaction was complete. The mixture was filtered through a pad of celite, and the celite pad washed with dichloromethane (4×200 mL). The filtrate was stirred vigorously with 0.5N NaOH (400 mL) for one hour. The layers were separated, the aqueous phase extracted with dichloromethane (2×100 mL), and the combined organics dried over sodium sulfate, filtered and concentrated to a waxy solid. The solid was dissolved in anhydrous ether (260 mL), cooled in an ice bath, seeded and heptane (540 mL) added dropwise with stirring for 2 h and allowed to stand in a cold room at ~5° C. for 2 days. The solid was collected, rinsed with cold heptane (40 mL) and air suction dried for 10 h affording 24.5 g of 1-Bromo-N-(methoxymethyl)-N-(4,5-dimethyl-3-isoxazolyl)benzenesulfonamide, 81.7%, AP 99.9+% as a white solid, mp 71–72° C. Concentration of the mother liquor to dryness and crystallization of the residue (5.02 g) from ether/heptane as above afforded a second crop of 1-Bromo-N-(methoxymethyl)-N-(4,5-dimethyl-3-isoxazolyl)benzenesulfonamide, 3.72 g, AP 99.9, 12.4%, mp 71–72° C. The $^1$H NMR and mass spectra were consistent with the assigned structure.

C. [2-[[(4,5-Dimethyl-3-isoxazolyl)(methoxymethyl)amino]sulfonyl]phenyl]boronic acid A 1 liter, 3-necked flask equipped with an overhead mechanical stirrer, addition funnel and thermocouple probe was charged with the aryl bromide described above (30.0 g, 80.2 mmol) and the flask was sparged with a slow stream of argon for 0.5 h. THF (400 mL) was added via cannula and the resulting solution was slowly cooled to an internal temperature of −100° C. n-BuLi (40.1 mL, 84.2 mmol) was added dropwise via an addition funnel over ~20 minutes with vigorous stirring, while maintaining the internal temperature between −99° C. and −101° C. The reaction mixture turned pale yellow, yellow and eventually orange. After the addition of n-BuLi was complete, the addition funnel was rinsed with THF (5 mL). The reaction was maintained at −100° C. for 20 minutes following which a solution of trimethylborate (18.2 mL, 160.4 mmol) in THF (136 mL) was added in a slow, steady stream via an addition funnel over 15 minutes. The internal temperature was maintained between −98° C. and −101° C. during the addition of the borate/THF solution. The reaction mixture turned light orange, yellow, and eventually pale yellow. The resultant solution was stirred at ~−100° C. for 1 h, following which it was warmed to ~−78° C. A solution of 3N HCl (158 mL) was added in a slow stream with vigorous stirring during which the reaction mixture exothermed to −35° C. The reaction mixture was warmed to 0° C. and stirred for 0.5 h. The reaction mixture (pH 0.1) was basified with 4N NaOH (130 mL) to pH ~12.2. The resulting solution was extracted with MTBE/hexanes (1:1, 2×300 mL), and the organic phase was washed with 0.5N NaOH (4×100 mL). The aqueous layers were pooled and washed with MTBE/hexanes (1/1, 2×300 mL). The aqueous layer (pH ~13.1) was acidified with 6.0N HCl (~85 mL) to a pH of ~1.0. The acidified solution was extracted with MTBE (4×300 mL). The organic layers were pooled, dried over Na$_2$SO$_4$, filtered and concentrated to afford 2-[[(4,5-Dimethyl-3-isoxazolyl)(methoxymethyl)amino]sulfonyl]phenyl]boronic acid as a pale yellow oil which solidified upon storing at 0–5° C. overnight. (25.4 g, 93%, HPLC area percent 93.1%). The $^1$H NMR and mass spectra were consistent with the assigned structure.

D. N-[methoxymethyl]-N-(4,5-dimethyl-3-isoxazolyl)-2-(4,4,5,5-tetramethyl-1,3,2-dioxaborolan-2-yl)benzenesulfonamide A 1-liter round bottomed flask equipped with magnetic stir bar, Dean-Stark trap and condenser was charged with the boronic acid as described above (25.0 g, 73.5 mmol), pinacol (9.1 g, 77.1 mmol), and toluene (1500 mL) and placed under an atmosphere of argon. The mixture was heated to vigorous reflux and water was collected in the Dean Stark trap over ~20 minutes. The mixture was heated at reflux for a total of 1.5 hours. Toluene (~75 mL) was then distilled off and the reaction mixture subsequently concentrated on a rotary evaporator for approximately 16 h to afford N-[methoxymethyl]-N-(4,5-dimethyl-3-isoxazolyl)-2-(4,4,5,5-tetramethyl-1,3,2-dioxaborolan-2-yl)benzenesulfonamide as a viscous, colorless oil (31.9 g, 103%, HPLC AP 97%). The $^1$H NMR and mass spectra were consistent with the assigned structure.

EXAMPLE 2

Preparation of Halophenyl Compound III

A. 4-Bromo-3-(dibromomethyl)benzoic acid

A 3 L 3-necked flask equipped with reflux condenser was charged with 3-methyl-4-bromo-benzoic acid (50 g), N-bromosuccinimide (41.4 g, 1 equiv), azobisisobutyronitrile (0.5 g) and triflourotoluene (750 mL). The headspace was purged with argon for 10 min. The flask was placed in a preheated oil bath at ~110° C., and stirred. Additional solid NBS (41.4 g, 1 equiv) and AIBN (250 mg) were added after 3–4 h. Additional solid NBS (41.4 g, 1 equiv) and AIBN (250 mg) after another 3–4 h. AIBN was added periodically (250 mg) every 3–4 h with heating and stirring under reflux. for 12–24 h until the side chainmonobromide:dibromide ratio is ~7:93 or better as judged by analytical HPLC. The mixture was cooled to RT with stirring, 250 mL heptane was added dropwise, and the mixture then stirred in ice-salt bath 2 h. The solid was collected and washed twice with cold heptane. The solid was air suction dried ~1 h. The solid was washed with warm (~70° C.) water (3×500 mL), stirring the filter cake each time. The solid was air suction dried 12 h. The weight of 4-Bromo-3-(dibromomethyl)benzoic acid was 72.5 g, 84%; HPLC and $^1$H NMR (DMSO-d6) give 96 area percent of sidechain dibromide, ~4 area percent monobromide.

The solid was dissolved in 1200 mL of hot n-butyl acetate, and filtered through a small pad of celite. The celite pad was rinsed with 100 mL of hot butyl acetate, the volume adjusted to 325 mL, and the mixture reheated to reflux to obtain a solution. Upon cooling to room temperature, crystals formed. The mixture was stirred, and heptane (650 mL) added at RT and then in an ice bath. The solid was collected and washed with ice cold heptane, and dried, affording the product 4-Bromo-3-(dibromomethyl)benzoic acid in ~70% yield. The $^1$H NMR and mass spectra were consistent with the assigned structure. The sidechain monobromide was typically present in <5%.

B. 4-Bromo-3-(dibromomethyl)benzoyl chloride

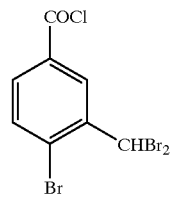

A 250 mL round bottom flask was charged with the 4-Bromo-3-(dibromomethyl)benzoic acid prepared as described above (114.6 g, 307 mmol) in anhydrous toluene (1.14 L) and anhydrous DMF (6.3 mL). The resulting suspension was stirred at RT under an argon atmosphere. Oxalyl chloride (29.5 mL, 338 mmol) was added dropwise. The reaction mixture became a clear yellow solution at the end of the reaction. HPLC indicated the reaction was complete in 2 hours. The solution was decanted away from a gummy oil deposited at the bottom of the reaction flask and the solution was concentrated on a rotary evaporator and then on a high vacuum pump overnight to dryness. The 4-Bromo-3-(dibromomethyl)benzoyl chloride was obtained as a light brown solid 115.02 g, 95.7% yield and area percent=93.5%. The $^1$H NMR spectrum was consistent with the assigned structure.

C. 2-[4-Bromo-3-(dibromomethyl)-phenyl]oxazole

A vessel was charged with 488, 4 ml of Sulfolane. 24.0

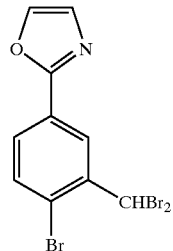

g of NaH (60% suspension in mineral oil) was added under an inert gas blanket. The suspension was agitated and heated to 50° C. In a separate vessel, 40, 7 g of 1.2.3-Triazole were dissolved in 244, 2 ml Sulfolane. The solution of 1.2.3-triazole was slowly added to the NaH suspension. Efficient agitation is essential. Evolution of hydrogen was observed. If hydrogen evolution gets too violent, addition has to be interrupted. After additon was complete agitation was continued at 50° C. for 1.5 hours. The 1.2.3 triazole-sodium suspension was cooled to 30° C.

The acid chloride prepared as described above was dissolved in 600 ml of Sulfolane. When all acid chloride was dissolved temperature was increased to 90–95° C. At this temperature the Na-triazole solution was slowly added. During addition the temperature was maintained at 95–100° C. The reaction was slightly exothermic. During addition slight gas evolution of nitrogen is observed. The additon required 60–90 minutes. When addition was complete, agitation was continued at 95–100° C. for 30 min. The mixture was cooled to 10° C., added slowly to an ice cold solution of 66.7 g of potassium carbonate in 2000 mL of water, maintaining the temperature below 10° C. After the potassium carbonate addition was complete, 660 mL of water were added and the mixture agitated for 30 min at 10° C. The crystals were isolated and dried by suction and washed with water. The cake was washed with 45° C. warm water to remove residual sulfolane. The yield of 2-[4-Bromo-3-(dibromomethyl)-phenyl]oxazole is 133.3 g.

133, 3 g of 2-[4-Bromo-3-(dibromomethyl)-phenyl] oxazole were dissolved in 666.7 mL of MeOH at reflux temperature, 20, 0 g of charcoal were added and reflux was continued for 5 min. The charcoal was filtered off at reflux temperature using a pad of hyflo filter aid. The cake was washed with 66.8 mL of hot MeOH. The solution was slowly cooled to ambient temperature. Crystallisation started at about 35° C. The mixture was agitated for one hour at ambient temperature then the temperature was lowered to 5° C. slowly and agitation continued for 1 hour.

66.7 mL of water were added slowly and the mixture agitated for an additional hour. The crystals were collected by suction filtration and dried to constant weight in vacuo. The yield of 2-[4-Bromo-3-(dibromomethyl)-phenyl] oxazole was 120 g. The $^1$H NMR and mass spectra were consistent with the assigned structure.

D. 2-[4-Bromo-3-(formyl)phenyl]oxazole

A 1000 mL round bottom flask was charged with the oxazole as described above (30 g, 75.8 mmol) in morpholine (67 mL, 757.6 mmol) and distilled water (17 mL). The resulting yellow solution was stirred under an argon atmosphere and was heated to 75° C. external temperature. Some solid precipitated out of the solution immediately and then slowly partially melted, resulting in a heterogeneous mixture. The reaction was monitored by HPLC and was complete in 2 hours. The reaction mixture was cooled to RT. Then HCl (1N, 760 mL) was added slowly and portionwise. The mixture was stirred at RT for 1 hour and in an ice bath for 2 hours. The solid was filtered, washed with H$_2$O (1×100 mL) and hot H$_2$O (3×100 mL). It was suction dried overnight to give 18.0 g of yellow solid, 94.1% yield and AP=99.6 (CPR-NB). The crude solid was combined with a previous batch (~1.8 g) and was dissolved in refluxing cyclohexane (470 mL). The hot solution was filtered to remove a small amount of insoluble solid. The filtration funnel was rinsed with hot cyclohexane (3×100 mL). The combined hot cyclohexane solution was stirred, cooled to RT and seeded. Crystallization occurred within 10 minutes. It was stirred at RT for 4–5 hours, stored in the cold room at 4° C. overnight and collected to give an off-white crystalline product. The solid was suction dried to afford 2-[4-Bromo-3-(formyl)phenyl]oxazole, 19.2 g, 91.2% yield and HPLC area percent 98.5. mp 100–104° C. The $^1$H NMR and mass spectra were consistent with the assigned structures. Elemental analysis for C$_{10}$H$_6$BrNO$_2$*0.1 H$_2$O*0.1 C$_6$H$_{12}$. C: Calc: 48.54, Found: 48.95; H: Calc: 2.84, Found: 2.94; N: Calc: 5.34, Found: 5.29. KF (H2O) Calc: 0.69, Found:0.63.

EXAMPLE 2A

Alternate Synthesis of Example 2D

A.

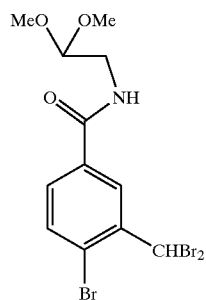

A 1 L round bottom flask was charged with potassium hydrogen carbonate (13.3 g, 132.3 mmol), water (220 mL) and acetone (150 mL). The resulting mixture was cooled to −10° C. to 0° C. in an ice/acetone bath. Aminoacetaldehyde dimethylacetal (14.5 mL, 133.1 mmol) was added and the mixture was stirred at −10° C. to 0° C. for 15 minutes. 4-Bromo-3-(dibromomethyl)benzoyl chloride (50.0 g, 127.8 mmol) in acetone (200 mL) was added dropwise in 0.5 hours under argon. During the course of the addition, the reaction mixture was seeded when cloudiness occurred. The resulting milk like suspension was stirred at 0° C. for 2.5 h. The solvent acetone was removed on a rotary evaporator. The solid was collected by filtration and was washed with water (50 mL×2). It was suction dried for 13 hours and vacuum oven dried for 6 hours at 60° C. to give the carboxamide aa a yellowish solid in 95.6% yield, HPLC area percent. The $^1$H NMR and mass spectra were consistent with the assigned structure.

B. 2-[4-Bromo-3-(dibromomethyl)-phenyl]-5-methoxy-oxazoline

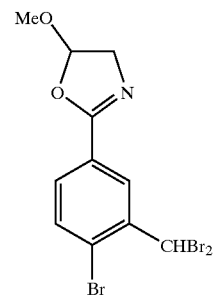

A 500 mL round bottom flask was charged with the amido acetal (30.3 g, 67.3 mmol), anhydrous toluene (200 mL) and diisopropylethylamine (47 mL, 269.8 mmol). The mixture was cooled to −10° C. to 0° C. in an ice/acetone bath under argon. Trifluoroboron etherate (33 mL) was added dropwise in 0.5 hours. A suspension was obtained. The suspension was warmed up to RT and stirred at RT for 1 hour. The suspension was heated at 60° C. for 3.5 hours. TLC indicated that the starting material was consumed. The mixture was cooled to RT and poured onto saturated sodium bicarbonate solution (1.2 L). The sodium bicarbonate mixture was stirred at RT for 0.5 hours (pH=9) and was filtered through a celite pad. The pad was rinsed with toluene (200 mL×3). Each rinsing was used to extract the aqueous phase. The toluene layers were combined and washed with saturated sodium bicarbonate solution (250 mL), water (250 mL×2) and brine (250 mL×2). It was dried over MgSO$_4$ (50 g) and charcoal (9 g) for 1 hour at RT. After filtration and concentration, 27.8 9 of 2-[4-Bromo-3-(dibromomethyl)-phenyl]-5-methoxy-oxazoline as a yellowish solid, which was used for the next reaction without further purification.

C. 2-[4-Bromo-3-(formyl)-phenyl]oxazole

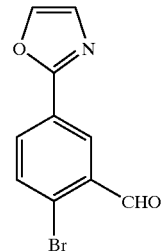

A 1 L round bottom flask was charged with 2-[4-bromo-3-(dibromomethyl)-phenyl]-5-methoxy-oxazoline (27.8 g, 67.1 mmol), DBU (24.1 mL, 161.2 mmol) and morpholine (56.4 mL, 646.7 mmol). The mixture was heated at 60° C. for 2.5 hours. HPLC indicated the starting material had disappeared. The reaction mixture was cooled to −10° C. to 0° C. in an ice/acetone bath. The stirring stopped. Potassium tert-butoxide (1 M in THF, 350 mL) was added dropwise in 0.5 hours. The stirring started after ~20 mL of potassium tert-butoxide THF solution was added. The reaction mixture was warmed up to RT and stirred at RT for 5 hours. It was put aside in a −40° C. freezer for 13 hours and then was stirred at RT for another 2 hours. The reaction mixture was cooled to −10° C. to 0° C. in an ice/acetone bath. HCl (6N, cold, 214 mL) was added dropwise in 15 minutes. The mixture was stirred at 0° C. to RT in 0.5 hours. It was transferred to a 2 L separatory funnel, diluted with EtOAc (300 mL) and water (300 mL). The aqueous layer was separated and extracted with EtOAc (300 mL×2). The organic layers were combined and the combined organic phase was washed with brine/1N HCl mixture (200 mL/30 mL), brine/water mixture (200 mL/30 mL×2) and brine (230 mL×2). It was dried over MgSO$_4$ (50 g) for 0.5 hours and concentrated to 21.3 g of semi solid. The crude semi solid was dissolved in warm THF (60 mL). The THF solution was added dropwise to a mixture of refluxing cyclohexane (600 mL) and charcoal (3.6 g). The mixture was stirred without heat for 0.5 hours and was heated to reflux. It was filtered through a celite pad and the pad was washed with a hot mixture of cyclohexane/THF (90 mL/9 mL×3). The filtrate was concentrated to 14.1 g of yellowish white solid. The charcoal treated crude product was dissolved in cyclohexane (300 mL) at reflux. Crystallization occurred upon cooling to RT. The mixture was stirred at RT for 4 hours and then at 4° C. for 13 hours. The 2-[4-Bromo-3-(formyl)-phenyl]oxazole was collected by filtration and was suction dried at RT for 13 h. It was obtained as an off-white solid in 72.3% yield, HPLC area percent 99.8. The $^1$H NMR and mass spectra were consistent with the assigned structure.

EXAMPLE 3

Preparation of Compound of Formula I

A. N-(4,5-Dimethyl-3-isoxazolyl)-2'-formyl-N-(methoxymethyl)-4'-oxazol-2-yl[1,1'-biphenyl] sulfonamide

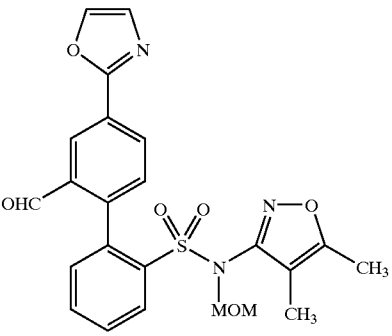

A 3-liter, 3-necked flask equipped with dropping funnel, condenser, overhead mechanical stirrer, and thermocouple was charged with Pd(OAc)$_2$ (0.56 g, 2.5 mmol), and Ph$_3$P (1.76 g, 6.7 mmol). The flask was purged with a slow bleed of Argon gas overnight. Toluene (125 mL) was added via syringe. The resulting pale yellow solution was stirred and heated at 73° C. to 75° C. in an oil bath for approximately 1 h 10 min. The color of the solution gradually changed from pale yellow to dark yellow to dark orange red and eventually, blood-red. The solution was was cooled to ~28° C.

A solution consisting of the pinacol boronate ester (11.6 g, 27.5 mmol) in toluene; 2-[4-Bromo-3-(formylphenyl) oxazole (12.6 g 50.0 mmol), ethanol (337.5 mL), and toluene (325 mL) was added via cannula. A thoroughly degassed solution of 2.0M Na$_2$CO$_3$ in water (150 mL) was added via cannula. The resultant mixture was stirred and the solution was heated to an internal temperature of approximately 72° C. to 74° C. The remaining pinacol boronate ester (11.6 g, 27.5 mmol) in toluene was added portionwise at intervals of ~20 minutes (~5.5 mmol of pinacol boronate, 7.9 mL every 20 minutes) for a total addition time of 2 h. The mixture was cooled to room temperature and combined with another small batch of crude product (prepared in an identical manner from 2.5 g of 2-[4-Bromo-3-(formylphenyl) oxazole). The layers were separated in a separatory funnel. The aqueous layer was extracted with EtOAc (4×120 mL). The organic extracts were combined, dried over MgSO$_4$ and filtered through a Teflon filter (pore size: 0.45 micron). The filtrate was concentrated to afford a reddish-brown oil (41.4 g).

The oil was dissolved in EtOAc (300 mL) and trithiocyanuric acid (TMT, 5.6 g, 31.6 mmol) was added. The mixture was heated at ~55° C. for 0.5 h, then charcoal[16] (27 g) was added. The resulting suspension was stirred for ~0.5 h at ~55° C. The suspension was cooled to 5° C. and maintained at that temperature for 15 minutes, then filtered through a 3" pad of celite. The celite pad was washed with EtOAc (3×200 mL). The filtrate was washed with 0.5N NaOH (4×150 mL) in a separatory funnel. The organic layer was then washed with brine (1×150 mL), dried over anhydrous MgSO$_4$, filtered and concentrated to give a yellow oil (35.1 g). The oil was dissolved in EtOAc (300 mL) and TMT (5.6 g, 31.6 mmol) was added. The mixture was heated at ~55° C. for 0.5 h, then charcoal (27 g) was added. The resulting suspension was stirred for ~0.5 h at ~55° C. The suspension was cooled to 5° C. and maintained at that temperature for 15 minutes, then filtered through a 3" pad of celite. The celite pad was washed with EtOAc (3×200 mL). The filtrate was washed with 0.5N NaOH (4×150 mL) in a separatory funnel. The organic layer was then washed with brine (1×150 mL), dried over anhydrous MgSO$_4$, filtered and concentrated to give crude N-(4,5-Dimethyl-3-isoxazolyl)-2'-formyl-N-(methoxymethyl)-4'-oxazol-2-yl[1,1'-biphenyl]sulfonamide as very pale yellow oil (30.8 g, 110%, HPLC area percent 85%).

B. N-(4,5-Dimethyl-3-isoxazolyl)-2'-formyl-4'-(2-oxazolyl) [1,1'-biphenyl]-2-sulfonamide

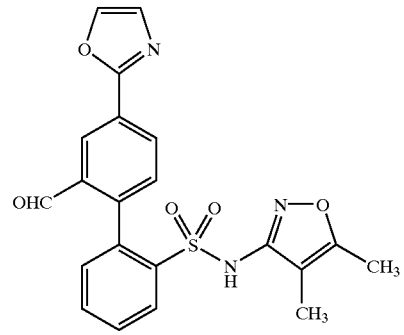

The unpurified biphenyl compound obtained as described above (30.4 g) was taken in a 2-liter round-bottom flask equipped with a condenser and dissolved in warm ethanol (300 mL). 6N aqueous HCl (300 mL) was added under an argon atmosphere. The solution was warmed and the internal temperature was maintained between 78° C. and 81° C. The progress of reaction was monitored by HPLC. After 2 h 45 min the reaction was judged complete by HPLC. A large quantity of the product had precipitated. The reaction mixture was cooled to ~74° C. Distilled water (207 mL) was added in a slow steady stream over 0.5 h during which time the internal temperature was maintained between 68 to 70° C. The resulting suspension was cooled to RT over 45 min following which the flask was cooled in an ice bath for 2 h with vigorous mechanical stirring. The crude product was collected by filtration on a sintered glass funnel, washed with a mixture of ethanol/water, and dried under house vacuum for 48 h, affording the crude N-(4,5-Dimethyl-3-isoxazolyl)-2'-formyl-4'-(2-oxazolyl) [1,1'-biphenyl]-2-sulfonamide product, 19.9 g, HPLC area percent 98%.

The crude solid (19.5 g) was suspended in distilled water (103 mL) and the suspension was cooled to ~10° C. 1N NaOH (92 mL) was added dropwise with vigorous mechanical stirring. The first formed milky emulsion became clear within 5–7 minutes. MTBE (60 mL) was added and the biphasic solution was stirred for 5 min. The layers were separated and the aqueous layer was diluted with ethanol (58 mL). The aqueous layer was acidified by the dropwise addition of 1N HCl (138 mL) over 45 min. The internal temperature was maintained between 18° C. to 22° C. during acidification. A white precipitate resulted and the resulting suspension was stirred at ~20° C. for 1 h. The product was collected by suction filtration and the filter cake washed with distilled water (80 mL). This was allowed to dry under house vacuum for 24 h, then in a vacuum oven (35° C.) for 16 h.

The crude product was suspended in acetonitrile (360 mL) at RT, then warmed to ~70° C. until a clear yellow solution was obtained. Hot distilled water (180 mL, ~75° C.) was added to the solution over 20 minutes with vigorous stirring. The product began to crystallize. The internal temperature was maintained at ~64° C.–67° C. with external heating. The resulting suspension was cooled to RT and stirred for 1 h, then placed in an ice-water bath for 8 h. The product was collected by vacuum filtration on a sintered glass funnel. The product was washed with an ice-cold solution of acetonitrile/water (1:1, 38 mL) and dried under house vacuum for 0.5 h, then in a vacuum oven at 30–35° C. overnight affording the product N-(4,5-Dimethyl-3-isoxazolyl)-2'-formyl-4'-(2-oxazolyl) [1,1'-biphenyl]-2-sulfonamide, 17.7 g, HPLC area percent 96.9%. The $^1$H NMR and mass spectra were consistent with the assigned structure.

C. N-(4,5-Dimethyl-3-isoxazolyl)-2'-[(methylamino)methyl]-4'-(2-oxazolyl) [1,1'-biphenyl]-2-sulfonamide, monohydrochloride

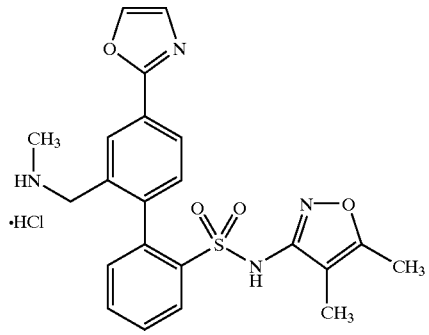

A 2 L three necked round bottom flask was charged with N-(4,5-Dimethyl-3-isoxazolyl)-2'-formyl-4'-(2-oxazolyl) [1,1'-biphenyl]-2-sulfonamide (15.0 g, 35.5 mmol). The reaction vessel was equipped with a mechanical stirrer, an argon line and a digital thermometer probe. Ethanol (195 mL) was added followed by glacial acetic acid (5.3 mL) and methylamine in ethanol (8.03 M, 15.6 mL). The resulting clear solution was stirred at room temperature. A thick white precipitate formed within 10 min. The suspension was stirred vigorously for 1 h following which sodium triacetoxyborohydride powder (22.6 g, 106 mmol) was added in one portion over 5 min. The inside walls of the flask were washed with ethanol (30 mL). A homogenous solution resulted within 15 min. The reaction mixture was stirred at RT for ~2 h, the reaction mixture was transferred to a 1 L flask and concentrated on a rotary evaporator. To the resulting thick slurry, 3N HCl (150 mL) was added dropwise over 10 min with rapid agitation. The suspension dissolved to give a clear pale yellow solution. Within minutes, a thick white precipitate formed. The suspension was stirred at RT for 1 h, then at 0–5° C., for 2.5 h. The flask was stored at 0–5° C. overnight. The suspension was stirred at 0–5° C. for 30 min and the precipitate collected by suction filtration on a sintered glass funnel. The crude product was washed with cold water (20 mL) and dried under house vacuum for 24 h.

The white solid (HPLC AP 97.6%) was dissolved in methanol (185 mL) at 50° C.–55° C. Charcoal (2.6 g) was added to the resulting solution and the suspension was stirred at 50° C.–55° C. for 1 h. The suspension was filtered through a pad of celite and the celite pad was washed with hot methanol (100 mL). The filtrate was concentrated to ~120 mL at which time some product had begun to precipitate. The residual suspension was heated to reflux to give a clear solution, and then cooled to RT with stirring over 1.5 h. The product began to crystallize. The suspension was stirred in an ice/water bath for 1.5 h, and stored at 0–5° C. for 16 h. The suspension was stirred at –24° C. to –27° C. for 3 h and the product collected by suction filtration on a sintered glass funnel. The product was washed with methanol (at ~–25° C.) and dried under house vacuum to give the product as the hydrochloride salt: N-(4,5-Dimethyl-3-isoxazolyl)-2'-[(methylamino)methyl]-4'-(2-oxazolyl) [1,1'-biphenyl]-2-sulfonamide, monohydrochloride (14.4 g, 85% crystallized yield from N-(4,5-Dimethyl-3-isoxazolyl)-2'-formyl-4'-(2-oxazolyl) [1,1'-biphenyl]-2-sulfonamide, HPLC area percent 98.8%. The $^1$H NMR and mass spectra were consistent with the assigned structure.

D. N-[[2'-[[(4,5-dimethyl-3-isoxazolyl)amino]sulfonyl]-4-(2-oxazolyl) [1,1'-biphenyl]-2-yl]methyl]-N,3,3-trimethylbutanamide

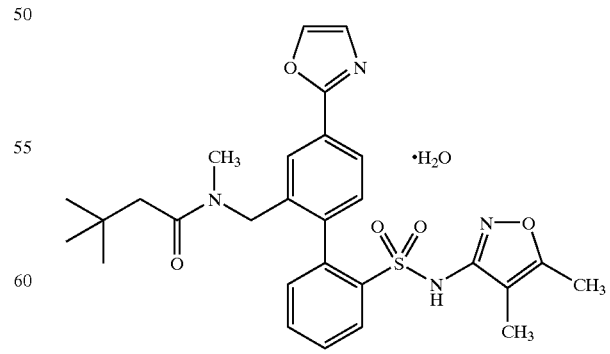

A 1-liter round-bottom flask was charged with the amine hydrochloride salt prepared as described above (14.2 g, 29.9 mmol). The flask was equipped with a Claisen head and mechanical stirrer. THF (220 mL), H$_2$O (248 mL) and 1N NaOH (142 mL) were added to the flask. The resulting suspension was stirred at RT until a clear, very pale, yellow homogenous solution was obtained. The reaction mixture was cooled to approximately −5° C. t-Butyl acetyl chloride (4.9 g, 5.1 mL, 35.9 mmol) was added dropwise via an addition funnel over 20 minutes, with vigorous stirring. The reaction mixture was stirred for a total of 1 h. The reaction mixture was concentrated on a rotary evaporator; approximately 195 mL of solvent was removed. The concentrated solution was cooled to 0° C., then acidified by the dropwise addition of 1N HCl (156 mL) over 10 minutes. A white precipitate resulted immediately. 6N HCl (10 mL) was then added to the suspension which was then stirred at 0–5° C. for 1.5 h. The crude product was collected by suction filtration through a sintered glass funnel. The solid was washed with cold water (250 mL) and allowed to dry under house vacuum to give the crude product carboxamide (17.4 g, 107%, HPLC area percent 99%).

The crude solid (16.73 g) was heated in isopropanol (250 mL) at 60° C. and filtered at 50° C. through a small bed of celite on a medium porosity glass frit. The celite was washed with isopropanol (50 mL×2) and the solvent removed on a rotary evaporator. The residue was dissolved in warm isopropanol (225 mL) and stirred in a an oil bath with internal temperature at ~58–60° C. and warm water (338 mL) was added dropwise maintaining the internal temperature at ~58–60° C. The solution was seeded at ~58° C., and slowly allowed to cool to RT with stirring over approximately 7 h, allowed to stand at RT overnight and then at 5° C. for 24 h. The solid was collected and rinsed with ice cold 1:1.5 isopropanol:water (30 mL) and air suction dried for 24 h affording 14.87 g, 92% of the product, N-[[2'-[[(4,5-dimethyl-3-isoxazolyl)amino]sulfonyl]-4-(2-oxazolyl) [1,1'-biphenyl]-2-yl]methyl]-N,3,3-trimethylbutanamide as the monohydrate, HPLC area percent 98.6, mp 116–118° C. The $^1$H NMR, infrared spectrum and mass spectrum were consistent with the assigned structure. Karl Fischer analysis indicated 3.4% water by weight, indicating a monohydrate. A crystalline anhydrate is obtained by crystallization from an isopropanol/water solvent mixture under similar conditions, mp 156–158° C. A second, different anhydrate is obtained from ethyl acetate/hexanes, mp 166–168° C.

What is claimed is:

1. A method for the preparation of a biphenyl sulfonamide of the following formula I

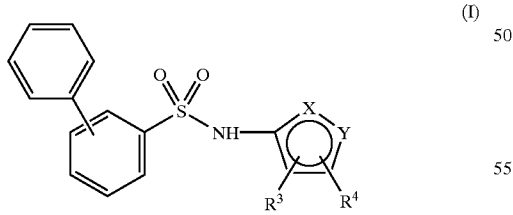

(I)

where the phenyl rings of the biphenyl group may independently be unsubstituted or substituted with one or more substituent groups,
enantiomers and diastereomers, and salts thereof,
wherein
one of X and Y is N and the other is O;
R$^3$ and R$^4$ are each directly bonded to a ring carbon and are each independently (a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aryloxy, any of which may be substituted with Z$^1$, Z$^2$ and Z$^3$;
(c) halo;
(d) hydroxyl;
(e) cyano;
(f) nitro;
(g) —C(O)H or —C(O)R$^5$;
(h) —CO$_2$H or —CO$_2$R$^5$;
(i) —Z$^4$—NR$^6$R$^7$;
—Z$^4$—N(R$^{10}$)—Z$^5$—NR$^8$R$^9$; or
(k) R$^3$ and R$^4$ together may also be alkylene or alkenylene, either of which may be substituted with Z$^1$, Z$^2$ and Z$^3$, completing a 4- to 8-membered saturated, unsaturated or aromatic ring together with the carbon atoms to which they are attached;

R$^5$ is alkyl, alkenyl, alkynyl, cycloalkyl, cycloalkylalkyl, cycloalkenyl, cycloalkenylalkyl, aryl or aralkyl, any of which may be substituted with Z$^1$, Z$^2$ and Z$^3$;

R$^6$, R$^7$, R$^8$, R$^9$ and R$^{10}$ are each independently
(a) hydrogen; or
(b) alkyl, cycloalkyl, cycloalkylalkyl, cycloalkenylalkyl, aryl or aralkyl, any of which may be substituted with Z$^1$, Z$^2$ and Z$^3$; or R$^6$ and R$^7$ together may be alkylene or alkenylene, either of which may be substituted with Z$^1$, Z$^2$ and Z$^3$, completing a 3- to 8-membered saturated or unsaturated ring together with the nitrogen atom to which they are attached; or any two of R$^8$, R$^9$ and R$^{10}$ together are alkylene or alkenylene, either of which may be substituted with Z$^1$, Z$^2$ and Z$^3$, completing a 3- to 8-membered saturated or unsaturated ring together with the atoms to which they are attached;

Z$^1$, Z$^2$ and Z$^3$ are each independently
(a) hydrogen;
(b) halo;
(c) hydroxy;
(d) alkyl;
(e) alkenyl;
(f) aryl;
(g) aralkyl;
(h) alkoxy;
(i) aryloxy;
(j) aryloxy;
(k) heterocycle, substituted heterocycle or heterocloxy;
(l) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
(m) oxo;
(n) nitro;
(o) cyano;
(p) —C(O)H or —C(O)Z$^6$;
(q) —CO$_2$H or —CO$_2$Z$^6$;
(r) —Z$^4$—NZ$^7$Z$^8$;
(s) —Z$^4$—N(Z$^{11}$)—Z$^5$—H;
(t) —Z$^4$—N(Z$^{11}$)—Z$^5$—Z$^6$; or
(u) —Z$^4$—N(Z$^{11}$)—Z$^5$—NZ$^7$Z$^8$;

$Z^4$ and $Z^5$ are each independently
(a) a single bond;
(b) $-Z^9-S(O)_n-Z^{10}-$;
(c) $-Z^9-C(O)-Z^{10}-$;
(d) $-Z^9-C(S)-Z^{10}-$;
(e) $-Z^9-O-Z^{10}-$;
(f) $-Z^9-S-Z^{10}-$;
(g) $-Z^9-O-C(O)-Z^{10}-$; or
(h) $-Z^9-C(O)-O-Z^{10}-$;

$Z^6$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy and trihaloalkoxy; or heterocycle or substituted heterocycle;

$Z^7$ and $Z^8$ are each independently hydrogen, alkyl, cycloalkyl, cycloalkylalkyl, cycloalkenylalkyl, aryl or aralkyl, or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is
(a) hydrogen; or
(b) alkyl, alkyl substituted with one, two or three halogens, cycloalkyl, cycloalkylalkyl, cycloalkenylalkyl, aryl or aralkyl;

or any two of $Z^7$, $Z^8$ and $Z^{11}$ together are alkylene or alkenylene, completing a 3- to 8-membered saturated or unsaturated ring together with the atoms to which they are attached;

each m is independently 1 or 2; and each n is independently 0, 1 or 2;

comprising the steps of
(a) contacting a pinacol ester of the formula II or salt thereof

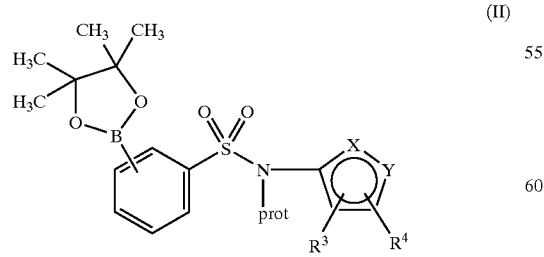

where the phenyl ring of said formula II may be further substituted, and where "prot" denotes an alkoxymethyl nitrogen-protecting group, with a compound of the formula III or salt thereof

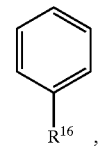

where $R^{16}$ is halogen or a group $-O-Q$ where Q is $-SO_2CF_3$, $-SO_2CH_3$, or

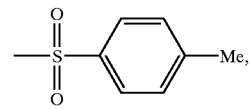

and where the phenyl ring of said formula III may be further substituted, in the presence of a palladium(0) catalyst and, optionally, a base, to form a compound of the formula IV or salt thereof

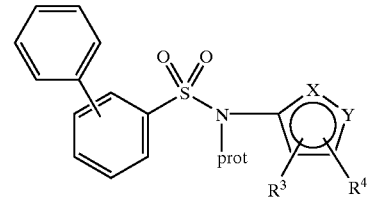

where the phenyl rings of the biphenyl group may independently be unsubstituted or substituted with one or more substituent groups; and (b) deprotecting the nitrogen of said compound of the formula IV or salt thereof to form said compound of the formula I or salt thereof.

2. The method of claim 1, for the preparation of a compound of the following formula Ia

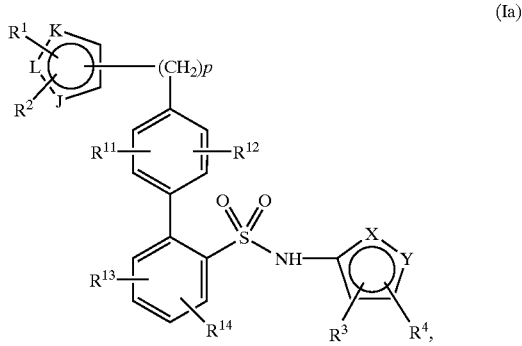

and enantiomers and diastereomers, and salts thereof, wherein $R^1$ and $R^2$ are each directly bonded to a ring carbon and are each independently selected from those groups (a) through (j) recited in claim 1 for $R^3$ and $R^4$;

$R^{11}$, $R^{12}$, $R^{13}$ and $R^{14}$ are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aryloxy, any of which may be substituted with $Z^1$, $Z^2$ and $Z^3$, (c) heterocycle, substituted heterocycle or heterocyclooxy;
(d) halo;
(e) hydroxyl;
(f) cyano;
(g) nitro;
(h) —C(O)H or —C(O)$R^5$;
(i) —$CO_2$H or —$CO_2R^5$;
(j) —SH, —S(O)$_n R^5$, —S(O)$_m$—OH, —S(O)$_m$—$OR^5$, —O—S(O)$_m$—$OR^5$, —O—S(O)$_m$OH or —O—S(O)$_m$—$OR^5$;
(k) —$Z^4$—$NR^6 R^7$; or
(l) —$Z^4$—N($R^{10}$)—$Z^5$—$NR^8 R^9$;

J is O, S, N or $NR^{15}$;

K and L are N or C, provided that at least one of K or L is C;

$R^{15}$ is hydrogen, alkyl, hydroxyethoxy methyl or methoxyethoxy methyl; and p is 0 or an integer from 1 to 2;

comprising the steps of:
(a) contacting a pinacol ester of the formula IIa or salt thereof

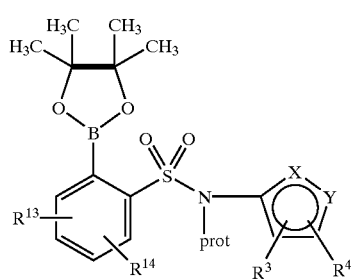
(IIa)

with a compound of the formula IIIa or salt thereof

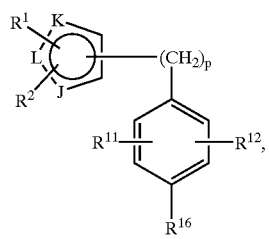
IIIa in the presence of a palladium(0) catalyst and, optionally, a base, to form a compound of the formula IVa or salt thereof

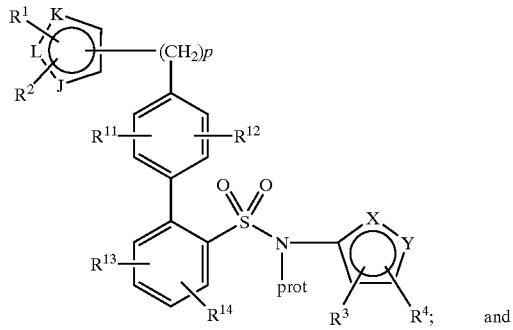
(IVa)

and (b) deprotecting the nitrogen of said formula IVa compound or salt thereof to form said compound of the formula Ia or salt thereof.

3. The method of claim 2, wherein said palladium(0) catalyst is a palladium (II) salt and triphenylphosphine.

4. The method of claim 3, wherein said palladium (II) salt is palladium acetate.

5. The method of claim 2, wherein said base is aqueous potassium carbonate or sodium carbonate.

6. The method of claim 2, wherein X is N, Y is O, and "prot" is methoxymethyl.

7. The method of claim 2, wherein the halo group in said compound of the formula IIIa or salt thereof is bromo, chloro, or iodo.

8. The method of claim 2, wherein said compound of the formula Ia or salt thereof is crystallized from solution subsequent to step (b).

9. The method of claim 2, wherein residual palladium is removed subsequent to step (a) by use of a chelating agent.

10. A method for the preparation of a biphenyl sulfonamide comprising contacting N-[methoxymethyl]-N-(4,5-dimethyl-3-isoxazolyl)-2-(4,4,5,5-tetramethyl-1,3,2-dioxaborolan-2-yl)benzenesulfanamide or a salt thereof, with 2-[4-Bromo-3-(formyl)phenyl]oxazole or a salt thereof.

11. The method of claim 1, wherein X is N and Y is O.

12. The method of claim 1, wherein prot" is methoxymethyl.

13. The method of claim 11, wherein prot" is methoxymethyl.

* * * * *